United States Patent
Heitsch et al.

(12)

(10) Patent No.: US 6,245,736 B1
(45) Date of Patent: *Jun. 12, 2001

(54) USE OF PEPTIDIC BRADYKININ ANTAGONISTS FOR THE TREATMENT AND PREVENTION OF ALZHEIMER'S DISEASE

(75) Inventors: Holger Heitsch, Mainz-Kastel; Stephan Henke, Hofheim; Gerhard Breipohl, Frankfurt; Jochen Knolle; Klaus Wirth, both of Kriftel; Gabriele Wiemer, Kronberg, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 08/949,496

(22) Filed: Oct. 14, 1997

(30) Foreign Application Priority Data

Oct. 14, 1996 (DE) .............................. 196 42 289

(51) Int. Cl.$^7$ .................................................. A61K 38/00
(52) U.S. Cl. ........................... 514/2; 514/15; 530/314
(58) Field of Search ................... 514/2, 15; 530/314

(56) References Cited

U.S. PATENT DOCUMENTS 5,952,346 * 9/1999 Heitsch et al. ................ 514/311

FOREIGN PATENT DOCUMENTS

| 0 370 453 | 5/1990 | (EP) . |
|---|---|---|
| 0 370 453 A2 | 5/1990 | (EP) . |
| 0 472 220 A1 | 2/1992 | (EP) . |
| 0 552 106 | 7/1993 | (EP) . |
| 0 578 521 | 1/1994 | (EP) . |
| 0 472 220 | 2/1992 | (WO) . |
| WO 92/17201 | 10/1992 | (WO) . |
| WO 92/18155 | 10/1992 | (WO) . |
| WO 93/11789 | 6/1993 | (WO) . |
| WO 94/06453 | 3/1994 | (WO) . |
| WO 94/08607 | 4/1994 | (WO) . |
| WO 94/11021 | 5/1994 | (WO) . |
| WO 94/19372 | 9/1994 | (WO) . |
| WO 95/07294 | 3/1995 | (WO) . |

OTHER PUBLICATIONS

Patel S., Journal of Geriatric Psychiatry and Neurology, vol. 8, pp. 81–95, 1995.*

Barger et al., Role of Cyclic GMP in the Regulation of Neuronal Calcium and Survival by Secreted Forms of β–Amyloid Precursor, Journal of Neurochemistry, vol. 64(5): 2087–2096 (1995).

Wirth et al., The bradykinin $B_2$ receptor antagonist WIN 64338 inhibits the effect of des–Arg$^9$–bradykinin in endothelial cells, European Journal of Pharmacology, Molecular Pharmacology Section 288 (1994) R1–R2.

Nitsch et al., Regulation of Proteolytic Processing of the Amyloid β–Protein Precursor by First Messengers, Arzneim.–Forsch./Drug Res. 45(I): 435–438 (1995).

Wiemer et al., Ramiprilat Enhances Endothelial Autacoid Formation by Inhibiting Breakdown of Endothelium–Derived Bradykinin, Hypertension, vol. 18(4): 558–563 (1991).

Rogers, J., Inflammation as a Pathogenic Mechanism in Alzheimer's Disease, Arzneim.–Forsch./Drug Res. vol. 45(1): 439–442 (1995).

Nakazawa et al., Activation of the Plasma Kinin–Forming Cascade by Aggregated β–Amyloid Protein, The Fifteenth International Conference on Kinins, (Abstract O–VI–1) Oct., 1998).

* cited by examiner

Primary Examiner—Dwayne C. Jones
Assistant Examiner—C. Delacroix-Muirheid
(74) Attorney, Agent, or Firm—Finnegan, Henderson, Farabow, Garrett and Dunner, L.L.P.

(57) ABSTRACT

The invention relates to the use of bradykinin antagonists for the production of pharmaceuticals for the treatment and prevention of Alzheimer's disease. Suitable bradykinin antagonists are peptides which inhibit the effects of the Alzheimer's protein amyloid (β/A4) on isolated endothelial cells. A particularly suitable peptide is H-D-Arg-Arg-Pro-Hyp-Gly-Thi-Ser-D-Tic-Oic-Arg-OH (HOE 140) and its physiologically tolerable salts.

15 Claims, No Drawings

USE OF PEPTIDIC BRADYKININ ANTAGONISTS FOR THE TREATMENT AND PREVENTION OF ALZHEIMER'S DISEASE

The present invention relates to the use of bradykinin antagonists for the treatment and/or prevention of Alzheimer's disease.

Bradykinin and related peptides are potent vasoactive, endogenous substances causing inflammation and pain. The use of bradykinin antagonists as agents for the control of conditions which are mediated, triggered and supported by bradykinin has been disclosed in EP-A-0 370 453, which is specifically incorporated by reference herein.

The importance of localized inflammation for the destructive changes in the brains of patients with Alzheimer's disease is increasingly recognized. Inflammatory changes lead to chronicity and to continuing destruction of the brain, and thus to severe dementia (J. Rogers, Inflammation as a pathogenic mechanism in Alzheimer's disease, Arzneimittelforschung 1995; 45 (3A),439–442). It was previously unknown that bradykinin, a strongly inflammatory mediator in the periphery, could play a part in Alzheimer's disease. This is to be attributed to the fact that there was no evidence of the release of bradykinin in the brains of patients with Alzheimer's disease. The inactive high molecular weight precursors from which bradykinin is released cannot pass directly into the brain (neuronal tissue), namely because of the low permeability of the blood-brain barrier.

Other investigations have shown that the Alzheimer's protein β/A4 can stimulate the release bradykinin from the endothelium of vascular walls. The essential pathological changes of Alzheimer's disease are ascribed to the Alzheimer proteinβ/A4. See, for example, C. L. Joachim and D. J. Selkoe, The seminal role of beta-amyloid in the pathogenesis of Alzheimer disease, Alzheimer Dis. Assoc. Disord., 1992 Spring, vol. 6(1), pp. 7–34. If the release of the inflammatory bradykinin is shown to be due to a mechanism which is specific for Alzheimer's disease, bradykinin will become a pathophysiological factor of first rank, via which the Alzheimer's protein can mediate its destructive action. This applies especially to inflammation, whose importance for the destructive changes is increasingly recognized, since bradykinin is one of the most potent endogenous inflammatory substances.

Beside the inflammatory action, bradykinin additionally has two other properties through which it can contribute to the destructive changes in Alzheimer's disease. Bradykinin stimulates CNS neurons. In the case of severe stimulation, this leads to calcium overloading of the affected cells, with subsequent cell death. On moderate stimulation, bradykinin only becomes a false transmitter, which inadequately stimulates neurons. Such an inadequate stimulation of neurons, which actually should not be stimulated at all, can sensitively interfere with the process of information processing in the brain and contribute to the typical brain power disorders, the latter mechanism, induced by moderate stimulation, appearing to be reversible.

As a vasoactive mediator, bradykinin increases, as is known, the permeability of the blood-brain barrier. This leads to the fact that the precursors of bradykinin can first pass from the blood vessels into the brain, in order to display their destructive action there.

Surprisingly, it has now been found that bradykinin antagonists are suitable agents for the treatment and prevention of Alzheimer's disease. This relates both to the intention to prevent progress of the disease and to treat symptoms which have already appeared. Moreover, bradykinin antagonists can also be used preventively in order to prevent the origination of Alzheimer's disease if in the future it should become possible by means of suitable diagnostic measures to predict a later outbreak of the disease.

Suitable compounds are bradykinin antagonists which inhibit the effects of the Alzheimer's protein amyloid (β/A4) on isolated endothelial cells.

Preferred bradykinin antagonists are, inter alia, the peptides of the formula (I):

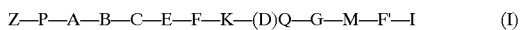

Z—P—A—B—C—E—F—K—(D)Q—G—M—F'—I        (I)

in which

Z is a$_1$) hydrogen, ($C_1$–$C_8$)-alkyl, ($C_1$–$C_8$)-alkanoyl, ($C_1$–$C_8$)-alkoxycarbonyl, ($C_3$–$C_8$)-cycloalkyl, ($C_4$–$C_9$)-cycloalkanoyl, or ($C_1$–$C_8$)-alkylsulfonyl, (1) in which 1, 2 or 3 hydrogen atoms in each of ($C_1$–$C_8$)-alkyl, ($C_1$–$C_8$)-alkanoyl, ($C_1$–$C_8$)-alkoxycarbonyl, ($C_3$–$C_8$)-cycloalkyl, ($C_4$–$C_9$)-cycloalkanoyl or ($C_1$–$C_8$)-alkylsulfonyl are optionally replaced by 1, 2 or 3 identical or different radicals selected from carboxyl, ($C_1$–$C_4$)-alkyl, ($C_1$–$C_8$)-alkylamino, ($C_6$–$C_{10}$)-aryl-($C_1$–$C_4$)-alkylamino, hydroxyl, ($C_1$–$C_4$)-alkoxy, halogen, Di-($C_1$–$C_8$)-alkylamino, Di-{($C_6$–$C_{10}$)-aryl-($C_1$–$C_4$)}-alkylamino, carbamoyl, phthalimido, 1,8-naphthalimido, sulfamoyl, ($C_1$–$C_4$)-alkoxycarbonyl, ($C_6$–$C_{14}$)-aryl, ($C_6$–$C_{14}$)-aryl-($C_1$–$C_5$)-alkyl, NHR(1), {($C_1$–$C_4$)-alkyl}NR(1) or {($C_6$–$C_{10}$)-aryl-($C_1$–$C_4$)-alkyl}NR(1), where R(1) is hydrogen or a urethane protective group, or (2) 1 or 2 hydrogen atoms in each of ($C_1$–$C_8$)-alkyl, ($C_1$–$C_8$)-alkanoyl, ($C_1$–$C_8$)-alkoxycarbonyl, ($C_3$–$C_8$)-cycloalkyl, ($C_4$–$C_9$)-cycloalkanoyl or ($C_1$–$C_8$)-alkylsulfonyl are replaced by 1 or 2 identical or different radicals selected from carboxyl, amino, ($C_1$–$C_8$)-alkylamino, hydroxyl, ($C_1$–$C_4$)-alkoxy, halogen, di-($C_1$–$C_8$)-alkylamino, carbamoyl, sulfamoyl, ($C_1$–$C_4$)-alkoxycarbonyl, ($C_6$–$C_{14}$)-aryl and ($C_6$–$C_{14}$)-aryl-($C_1$–$C_5$)-alkyl, and 1 hydrogen atom in each of ($C_1$–$C_8$)-alkyl, ($C_1$–$C_8$)-alkanoyl, ($C_1$–$C_8$)-alkoxycarbonyl, ($C_3$–$C_8$)-cycloalkyl, ($C_4$–$C_9$)-cycloalkanoyl, or ($C_1$–$C_8$)-alkylsulfonyl is optionally replaced by a radical selected from ($C_3$–$C_8$)-cycloalkyl, ($C_1$–$C_6$)-alkylsulfonyl, ($C_1$–$C_6$)-alkylsulfinyl, ($C_6$–$C_{14}$)-aryl-($C_1$–$C_4$)-alkylsulfonyl, ($C_6$–$C_{14}$)-aryl-($C_1$–$C_4$)-alkylsulfinyl, ($C_6$–$C_{14}$)-aryl, ($C_6$–$C_{14}$)-aryloxy, ($C_3$–$C_{13}$)-heteroaryl and ($C_3$–$C_{13}$)-heteroaryloxy, a$_2$) ($C_6$–$C_{14}$)-aryl, ($C_7$–$C_{15}$)-aroyl, ($C_6$–$C_{14}$)-arylsulfonyl, ($C_3$–$C_{13}$)-heteroaryl, or ($C_3$–$C_{13}$)-heteroaroyl, or a$_3$) carbamoyl which can optionally be substituted on the nitrogen by ($C_1$–$C_8$)-alkyl, ($C_6$–$C_{14}$)-aryl or ($C_6$–$C_{14}$)-aryl-($C_1$–$C_5$)-alkyl, where for the radicals defined under a$_1$), a$_2$) and a$_3$) the aryl, heteroaryl, aroyl, arylsulfonyl and heteroaroyl groups are optionally substituted by 1, 2, 3 or 4 radicals selected from carboxyl, amino, nitro, ($C_1$–$C_8$)-alkylamino, hydroxyl, ($C_1$–$C_6$)-alkyl, ($C_1$–$C_6$)-alkoxy, ($C_6$–$C_{14}$)-aryl, ($C_7$–$C_{15}$)-aroyl, halogen, cyano, di-($C_1$–$C_8$)-alkylamino, carbamoyl, sulfamoyl and ($C_1$–$C_6$)-alkoxycarbonyl;

P is a direct bond or a radical of the formula (II), $$-NR(2)-(U)-CO- \tag{II}$$

in which
R(2) is hydrogen, methyl or a urethane protective group,
U is $(C_3-C_8)$-cycloalkylidene, $(C_6-C_{14})$-arylidene, $(C_3-C_{13})$-heteroarylidene, $(C_6-C_{14})$-aryl-$(C_1-C_6)$-alkylidene, each of which can optionally be substituted, or is $\{CHR(3)\}_n$, where n is 1–8, preferably 1–6, and
R(3) independently of one another is hydrogen, $(C_1-C_6)$-alkyl, $(C_3-C_8)$-cycloalkyl, $(C_6-C_{14})$-aryl or $(C_3-C_{13})$-heteroaryl, which with the exception of the hydrogen are in each case optionally monosubstituted by amino, substituted amino, amidino, substituted amidino, hydroxyl, carboxyl, carbamoyl, guanidino, substituted guanidino, ureido, substituted ureido, mercapto, methylmercapto, phenyl, 4-chlorophenyl, 4-fluorophenyl, 4-nitrophenyl, 4-methoxyphenyl, 4-hydroxyphenyl, phthalimido, 1,8-naphthalimido, 4-imidazolyl, 3-indolyl, 2-thienyl, 3-thienyl, 2-pyridyl, 3-pyridyl or cyclohexyl,
where the substituted amino preferably is —N(A')—Z, the substituted amidino preferably is —(NH)C—NH—Z, the substituted guanidino preferably is —N(A')—C(N(A'))—NH—Z and the substituted ureido preferably is —C(O)—N(A')—Z, in which A' independently of one another is Z, Z being defined as under $a_1$) or $a_2$),
or in which
U is $\{CHR(3)\}_n$, where n is 1–8, preferably 1–6, and R(2) and R(3) together with the atoms carrying these radicals form a mono-, bi- or tricyclic ring system having 2 to 15 carbon atoms;
A is defined as P;
B is a basic amino acid in the L or D configuration, which can be substituted in the side chain;
C is a compound of the formula (IIIa) or (IIIb)

$$G'-G'-Gly \tag{IIIa}$$

$$G'-NH-(CH_2)_p-CO \tag{IIIb}$$

in which
p is 2 to 8, and
G' independently of one another is a radical of the formula (IV)

$$-NR(4)-CHR(5)-CO- \tag{IV}$$

in which
R(4) and R(5) together with the atoms carrying these radicals form a heterocyclic mono-, bi- or tricyclic ring system having 2 to 15 carbon atoms;
E is the radical of a neutral, acidic or basic, aliphatic or alicyclic-aliphatic amino acid;
F is the radical of a neutral, acidic or basic, aliphatic or aromatic amino acid which can be substituted in the side chain, or a direct bond;
K is the radical —NH—$(CH_2)_x$—CO— where x=1–4 or a direct bond;
(D)Q is D-Tic, D-Phe, D-Oic, D-Thi or D-Nal, each of which can optionally be substituted by halogen, methyl or methoxy, or a radical of the formula (V) below

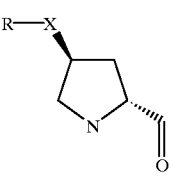

in which
X is oxygen, sulfur or a direct bond, and
R is hydrogen, $(C_1-C_8)$-alkyl, $(C_3-C_8)$-cycloalkyl, $(C_6-C_{14})$-aryl or $(C_6-C_{14})$-aryl-$(C_1-C_4)$-alkyl,
where the alicycle of formula (V) can optionally be substituted by halogen, methyl or methoxy;
G is defined as G' above or is a direct bond;
M is defined as F;
F' is defined as F, is a radical —NH—$(CH_2)_q$—, where q=2 to 8, or, if G is not a direct bond, is a direct bond; and
I is —OH, —$NH_2$ or $NHC_2H_5$, wherein I is not directly bonded to D(Q);
or a physiologically tolerable salt thereof.

Suitable bradykinin antagonists and their preparation are described, for example, in the Patent Applications WO 95/07294 (Scios Nova, Pseudopeptides), WO 94/08607 (Scios Nova, Pseudopeptides), WO 94/06453 (Stewart, aliphatic amino acid in 5-position), WO 93/11789 (Nova), EP-A 552 106 (Adir), EP-A 578 521 (Adir), WO 94/19372 (Scios Nova, Cyclopeptides), EP-A 370 453 (Hoechst), EP-A 472 220 (Syntex), WO 92/18155 (Nova), WO 92/18156 (Nova), WO 92/17201 (Cortech) and WO 94/11021 (Cortech; bradykinin antagonists of the formula $X(BKA)_n$, in which X is a connecting link, BKA is the peptide chain of a bradykinin antagonist and n is an integer greater than 1; bradykinin antagonists of the formula X(BKA); and bradykinin antagonists of the formula (Y)(X)(BKA) where Y is a ligand which is an antagonist or an agonist for a nonbradykinin receptor), the disclosures of all of which are specifically incorporated by reference herein.

Particularly suitable peptides of the formula (I) are those in which:
Z is as defined above under $a_1$), $a_2$) or $a_3$);
P is a bond or a radical of the formula (II)

$$-NR(2)-(U)-CO- \tag{II}$$

where
U is CHR(3),
R(3) is as defined above, and
R(2) is H or $CH_3$, wherein R(2) and R(3) together with the atoms carrying these radicals can form a mono-, bi- or tricyclic ring system having 2 to 15 carbon atoms; and
A is a direct bond.

In particular, preferred compounds of the formula (I) are those in which:
Z is as defined above under $a_1$), $a_2$) or $a_3$);
P is a bond or a radical of the formula (II)

$$-NR(2)-(U)-CO- \tag{II}$$

where
R(2) is H or $CH_3$,
U is CHR(3) and
R(3) independently of one another is hydrogen, $(C_1-C_6)$-alkyl, $(C_3-C_8)$-cycloalkyl, $(C_6-C_{14})$- aryl, (C$_3$–C$_{13}$)-heteroaryl, which with the exception of the hydrogen in each case are optionally monosubstituted by amino, substituted amino, hydroxyl, carboxyl, carbamoyl, guanidino, substituted guanidino, ureido, mercapto, methylmercapto, phenyl, 4-chlorophenyl, 4-fluorophenyl, 4-nitrophenyl, 4-methoxyphenyl, 4-hydroxyphenyl, phthalimido, 4-imidazolyl, 3-indolyl, 2-thienyl, 3-thienyl, 2-pyridyl, 3-pyridyl or cyclohexyl, where substituted amino preferably is —N(A')—Z and substituted guanidino preferably is —N(A')—C(N (A'))—NH—Z, in which A' independently of one another is Z, where Z is as defined under a$_1$) or a$_2$), or in which R(2) and R(3) together with the atoms carrying these radicals form a mono-, bi- or tricyclic ring system having 2 to 15 carbon atoms;

A is a bond; and (D)Q is D-Tic.

The following are preferably suitable:

H-D-Arg-Arg-Pro-Hyp-Gly-Thi-Ser-D-Tic-Oic-Arg-OH (HOE 140);

para-guanidobenzoyl-Arg-Pro-Hyp-Gly-Thi-Ser-D-Tic-Oic-Arg-OH;

H-D-Arg-Arg-Pro-Hyp-Gly-Phe-Ser-D-HypE(transpropyl)-Oic-Arg-OH;

H-D-Arg-Arg-Pro-Hyp-Gly-Cpg-Ser-D-Cpg-Cpg-Arg-OH;

H-D-Arg-Arg-Pro-Pro-Gly-Thi-Ser-D-Tic-Oic-Arg-OH;

H-Arg(Tos)-Pro-Hyp-Gly-Thi-Ser-D-Tic-Oic-Arg-OH;

H-Arg(Tos)-Pro-Hyp-Gly-Phe-Ser-D-Tic-Oic-Arg-OH;

H-D-Arg-Arg-Pro-Hyp-Gly-Phe-Ser-D-Tic-Oic-Arg-OH;

Fmoc-D-Arg-Arg-Pro-Hyp-Gly-Thi-Ser-D-Tic-Oic-Arg-OH;

Fmoc-Aoc-D-Arg-Arg-Pro-Hyp-Gly-Thi-Ser-D-Tic-Oic-Arg-O H;

Fmoc-ε-aminocaproyl-D-Arg-Arg-Pro-Hyp-Gly-Thi-Ser-D-Tic-Oic-Arg-OH;

benzoyl-D-Arg-Arg-Pro-Hyp-Gly-Thi-Ser-D-Tic-Oic-Arg-OH;

cyclohexylcarbonyl-D-Arg-Arg-Pro-Hyp-Gly-Thi-Ser-D-Tic-Oic-Arg-OH;

Fmoc-Aeg(Fmoc)-D-Arg-Arg-Pro-Hyp-Gly-Thi-Ser-D-Tic-Oic-Arg-OH;

Fmoc-Aeg(Fmoc)-Arg-Pro-Hyp-Gly-Thi-Ser-D-Tic-Oic-Arg-OH;

indol-3-yl-acetyl-D-Arg-Arg-Pro-Hyp-Gly-Thi-Ser-D-Tic-Oic-Arg-OH;

dibenzylacetyl-D-Arg-Arg-Pro-Hyp-Gly-Thi-Ser-D-Tic-Oic-Arg-OH;

and their physiologically tolerable salts.

The following are particularly suitable:

H-D-Arg-Arg-Pro-Hyp-Gly-Thi-Ser-D-Tic-Oic-Arg-OH (HOE 140);

para-guanidobenzoyl-Arg-Pro-Hyp-Gly-Thi-Ser-D-Tic-Oic-Arg-OH;

and their physiologically tolerable salts.

H-D-Arg-Arg-Pro-Hyp-Gly-Thi-Ser-D-Tic-Oic-Arg-OH (HOE 140) and its physiologically tolerable salts are very particularly suitable.

Preferred salts are alkali metal or alkaline earth metal salts, salts with physiologically tolerable amines and salts with inorganic or organic acids such as, for example, HCl, HBr, H$_2$SO$_4$, H$_2$PO$_4$, maleic acid, fumaric acid, citric acid, tartaric acid and acetic acid.

Administration can be carried out enterally, parenterally, such as, for example, subcutaneously, i.m. or i.v., nasally, rectally or by inhalation. The dose of the active compound depends on the body weight, age and on the manner of administration.

The pharmaceutical preparations of the present invention are prepared in dissolving, mixing, granulating, tabletting or sugar-coating processes known per se.

For parenteral administration, the active compounds or their physiologically tolerable salts are brought into solution, suspension or emulsion, if desired using the pharmaceutically customary auxiliaries, for example for isotonicization or pH adjustment, and solubilizers, emulsifiers or other auxiliaries.

For the pharmaceuticals described, the use of injectable delayed release preparations for subcutaneous or intramuscular administration is also efficient. The pharmaceutical forms used can be, for example, oily crystal suspensions, microcapsules, microparticles, nanoparticles or implants, the latter being constructed from tissue-compatible polymers, in particular biodegradable polymers, such as, for example, on the basis of polylactic acid/polyglycolic acid copolymers. Other conceivable polymers are polyamides, polyesters, polyacetates or polysaccharides.

For the oral administration form, the active compounds are mixed with the additives customary for this purpose such as excipients, stabilizers or inert diluents and are brought by customary methods into suitable administration forms, such as tablets, coated tablets, dry-filled capsules, aqueous, alcoholic or oily suspensions or aqueous, alcoholic or oily solutions. Inert excipients which can be used are, for example, gum arabic, magnesium oxide, magnesium carbonate, potassium phosphate, lactose, glucose, magnesium stearyl fumarate or starch, in particular corn starch. The preparation of solid pharmaceutical forms in this case can take place both as dry and moist granules. Suitable oily excipients or solvents are, for example, vegetable or animal oils, such as sunflower oil and cod liver oil.

Oral delayed release preparations or preparations having enteric coatings are also conceivable. Delayed release preparations can be constructed on the basis of fat, wax or polymer embeddings. Multilayer or press-coated tablets or pellets are also possible here.

For the pharmaceuticals described, administration to mucous membranes to achieve systemically active levels is also efficient. This relates to the possibility of use intranasally, by inhalation and rectally.

For the intranasal administration form, the compounds are mixed with the additives customary for this purpose such as stabilizers or inert diluents and are brought by customary methods into suitable administration forms, such as powder, aqueous, alcoholic or oily suspensions or aqueous, alcoholic or oily solutions. Chelating agents, such as ethylenediamine-N,N,N',N'-tetraacetic acid and buffers such as acetic acid, phosphoric acid, citric acid, tartaric acid and their salts can be added to aqueous intranasal preparations. Multidose containers contain preservatives such as benzalkonium chloride, chlorobutanol, chlorhexidine, sorbic acid, benzoic acid, PHB estes or organomercury compounds.

The administration of the nasal solutions can take place by means of metered atomizers or as nasal drops with a viscosity-enhancing component or nasal gels or nasal creams.

For administration by inhalation, atomizers or pressurized gas packs using inert carrier gases can be used.

For the administration of powders for nasal or pulmonary inhalation, special applicators are necessary.

The efficacious dose is at least 0.001 mg/kg/day, preferably at least 0.01 mg/kg/day, at most 5 mg/kg/day, preferably 0.03 to 1 mg/kg/day of body weight, depending on the degree of severity of the symptoms, based on an adult of body weight 75 kg.

The abbreviations used for amino acids correspond to the three letter code customary in peptide chemistry, as is described in Europ. J. Biochem 138,9 (1984). Other abbreviations used are listed below:

Aeg N-(2-aminoethyl)glycine
Cpg cyclopentylglycyl
Fmoc 9-fluoroenylmethoxycarbonyl
Nal 2-naphthylalanyl
Oic cis,endo-octahydroindole-2-carbonyl
Thi 2-thienylalanyl
Tic 1,2,3,4-tetrahydroisoquinolin-3-ylcarbonyl

EXAMPLE 1

Action of the compounds of the formula (I) on cGMP production stimulated by the Alzheimer protein β/A4 in endothelial cell cultures Test Systems Bovine aortic endothelial cell cultures (BAECs=bovine aortic endothelial cells), intravascular coronary rat endothelial cell cultures (RMCECs=rat microvascular coronary endothelial cells) and human umbilical vein endothelial cell cultures (HUVECs=human umbilical vein endothelial cells)

Method

Determination of the effect of bradykinin antagonists of the formula (I) on the production of cGMP stimulated by administration of 0.1 and 1 $\mu$mol/l of the Alzheimer protein β/A4 in endothelial cell cultures of various species and organs.

cGMP cyclic guanosine monophosphate

It has been adequately shown that endothelial cells are a suitable test system for the demonstration of an action and release of bradykinin (G. Wiemer et al., Hypertension 1991; 18:558–563). In endothelial cells, bradykinin leads to an increase in the production of cGMP, which is determined by means of a radioimmunoassay. Increase in the formation of cGMP by bradykinin is an indicator of a release of NO (nitrogen monoxide) from endothelial cells.

Experiment

Stimulation of cGMP production by βA(1–40) and inhibitory effect of the bradykinin antagonist HOE 140 ($10^{-7}$ mol/l) in 3 different types of endothelial cells:

|  | pmol/mg of protein | | |
| --- | --- | --- | --- |
| Endothelial cell type | BAECs | RMCECs | HUVECs |
| Basal cGMP production | 2.2 ± 0.35 | 0.2 ± 0.07 | 4.75 ± 0.4 |
| BK $10^{-8}$ mol/l | 8.8 ± 0.34 | 1.13 ± 0.2 | 11.46 ± 2 |
| BK $10^{-8}$ mol/l + HOE 140 | 2.2 ± 0.2 | 0.22 ± 0.02 | 3.45 ± 0.45 |
| βA (1–40) $10^{-7}$ mol/l | 5.9 ± 0.23 | 0.59 ± 0.07 | 14.07 ± 1.6 |
| βA (1–40) $10^{-7}$ mol/l + HOE 140 | 2.2 ± 0.28 | 0.34 ± 0.02 | 4.0 ± 0.46 |
| βA (1–40) $10^{-6}$ mol/l | 4.6 ± 0.13 | 0.74 ± 0.09 | 15.3 ± 1.9 |
| βA (1–40) $10^{-6}$ mol/l + HOE 140 | 2.2 ± 0.2 | 0.32 ± 0.05 | 5.3 ± 0.49 |

Results

The simultaneous incubation of the above mentioned cell cultures of different species and organs with HOE 140 as a representative example of the compounds of the formula (I) in a concentration of 0.1 $\mu$mol/l prevents the stimulation of the production of cGMP induced by the β/A4 protein.

Assessment

The experiment carried out indicates that the action of the Alzheimer protein β/A4 on the production of cGMP is mediated by a binding of bradykinin to its cell receptors. Endothelial cell cultures serve here as an indicator that the action of β/A4 is mediated by bradykinin. The endothelial cells here are, however, not only the indicator system for an action on bradykinin receptors, but also the effector organ in Alzheimer's disease. Endothelial cells are constituents of the blood vessels and line the latter. The blood vessels themselves are severely affected by deposits of the Alzheimer protein amyloid (β/A4) in Alzheimer's disease in addition to neuronal tissue. Endothelial cells are responsible for an increase in the permeability of the blood-brain barrier induced by bradykinin.

We claim:

1. A method for the treatment or prevention of the progress of Alzheimer's disease comprising the step of administering to a host in recognized need of such treatment an amount of a bradykinin antagonist, or a physiologically tolerable salt thereof, effective to achieve said treatment.

2. The method as claimed in claim 1 wherein said bradykinin antagonist is a peptide, or a physiologically tolerable salt thereof.

3. The method as claimed in claim 2 wherein said bradykinin antagonist is a peptide of the formula (I):

$$Z\text{—}P\text{—}A\text{—}B\text{—}C\text{—}E\text{—}F\text{—}K\text{—}(D)Q\text{—}G\text{—}M\text{—}F'\text{—}I \qquad (I)$$

in which

Z is $a_1$) hydrogen, $(C_1\text{–}C_8)$-alkyl, $(C_1\text{–}C_8)$-alkanoyl, $(C_1\text{–}C_8)$-alkoxycarbonyl, $(C_3\text{–}C_8)$-cycloalkyl, $(C_4\text{–}C_9)$-cycloalkanoyl, or $(C_1\text{–}C_8)$-alkylsulfonyl, (1) in which 1, 2 or 3 hydrogen atoms in each of $(C_1\text{–}C_8)$-alkyl, $(C_1\text{–}C_8)$-alkanoyl, $(C_1\text{–}C_8)$-alkoxycarbonyl, $(C_3\text{–}C_8)$-cycloalkyl, $(C_4\text{–}C_9)$-cycloalkanoyl or $(C_1\text{–}C_8)$-alkylsulfonyl are optionally replaced by 1, 2 or 3 identical or different radicals selected from carboxyl, $(C_1\text{–}C_4)$-alkyl, $(C_1\text{–}C_8)$-alkylamino, $(C_6\text{–}C_{10})$-aryl-$(C_1\text{–}C_4)$-alkylamino, hydroxyl, $(C_1\text{–}C_4)$-alkoxy, halogen, Di-$(C_1\text{–}C_8)$-alkylamino, Di-$\{(C_6\text{–}C_{10})$-aryl-$(C_1\text{–}C_4)\}$-alkylamino, carbamoyl, phthalimido, 1,8-naphthalimido, sulfamoyl, $(C_1\text{–}C_4)$-alkoxycarbonyl, $(C_6\text{–}C_{14})$-aryl, $(C_6\text{–}C_{14})$-aryl-$(C_1\text{–}C_5)$-alkyl, NHR(1), $\{(C_1\text{–}C_4)$-alkyl$\}$NR(1) or $\{(C_6\text{–}C_{10})$-aryl-$(C_1\text{–}C_4)$-alkyl$\}$NR(1), where R(1) is hydrogen or a urethane protective group, or (2) 1 or 2 hydrogen atoms in each of $(C_1\text{–}C_8)$-alkyl, $(C_1\text{–}C_8)$-alkanoyl, $(C_1\text{–}C_8)$-alkoxycarbonyl, $(C_3\text{–}C_8)$-cycloalkyl, $(C_4\text{–}C_9)$-cycloalkanoyl or $(C_1\text{–}C_8)$-alkylsulfonyl are replaced by 1 or 2 identical or different radicals selected from carboxyl, amino, $(C_1\text{–}C_8)$-alkylamino, hydroxyl, $(C_1\text{–}C_4)$-alkoxy, halogen, di-$(C_1\text{–}C_8)$-alkylamino, carbamoyl, sulfamoyl, $(C_1\text{–}C_4)$-alkoxycarbonyl, $(C_6\text{–}C_{14})$-aryl and $(C_6\text{–}C_{14})$-aryl-$(C_1\text{–}C_5)$-alkyl, and 1 hydrogen atom in each of $(C_1\text{–}C_8)$-alkyl, $(C_1\text{–}C_8)$-alkanoyl, $(C_1\text{–}C_8)$-alkoxycarbonyl, $(C_3\text{–}C_8)$-cycloalkyl, $(C_4\text{–}C_9)$-cycloalkanoyl, or $(C_1\text{–}C_8)$-alkylsulfonyl is optionally replaced by a radical selected from $(C_3\text{–}C_8)$-cycloalkyl, $(C_1\text{–}C_6)$-alkylsulfonyl, $(C_1\text{–}C_6)$-alkylsulfinyl, $(C_6\text{–}C_{14})$-aryl-$(C_1\text{–}C_4)$-alkylsulfonyl, $(C_6\text{–}C_{14})$-aryl-$(C_1\text{–}C_4)$-alkylsulfinyl, $(C_6\text{–}C_{14})$-aryl, $(C_6\text{–}C_{14})$-aryloxy, $(C_3\text{–}C_{13})$-heteroaryl and $(C_3\text{–}C_{13})$-heteroaryloxy, $a_2$) $(C_6\text{–}C_{14})$-aryl, $(C_7\text{–}C_{15})$-aroyl, $(C_6\text{–}C_{14})$-arylsulfonyl, $(C_3\text{–}C_{13})$-heteroaryl, or $(C_3\text{–}C_{13})$-heteroaroyl, or $a_3$) carbamoyl which can optionally be substituted on the nitrogen by $(C_1\text{–}C_8)$-alkyl, $(C_6\text{–}C_{14})$-aryl or $(C_6\text{–}C_{14})$-aryl-$(C_1\text{–}C_5)$-alkyl, where for the radicals defined under $a_1$), $a_2$) and $a_3$) the aryl, heteroaryl, aroyl, arylsulfonyl and heteroaroyl groups are optionally substituted by 1, 2, 3 or 4 radicals selected from carboxyl, amino, nitro, $(C_1\text{–}C_8)$-alkylamino, hydroxyl, $(C_1\text{–}C_6)$-alkyl, $(C_1\text{–}C_6)$-alkoxy, $(C_6\text{–}C_{14})$-aryl, $(C_7\text{–}C_{15})$-aroyl, halogen, cyano, di-$(C_1\text{–}C_8)$-alkylamino, carbamoyl, sulfamoyl and $(C_1\text{–}C_6)$-alkoxycarbonyl;

P is a direct bond or a radical of the formula (II), $$\text{—NR(2)—(U)—CO—} \qquad (II)$$

in which

R(2) is hydrogen, methyl or a urethane protective group,

U is $(C_3\text{–}C_8)$-cycloalkylidene, $(C_6\text{–}C_{14})$-arylidene, $(C_3\text{–}C_{13})$-heteroarylidene, $(C_6\text{–}C_{14})$-aryl-$(C_1\text{–}C_6)$-alkylidene, each of which can optionally be substituted, or is $\{CHR(3)\}_n$, where n is 1–8, and R(3) independently of one another is hydrogen, $(C_1\text{–}C_6)$-alkyl, $(C_3\text{–}C_8)$-cycloalkyl, $(C_6\text{–}C_{14})$-aryl or $(C_3\text{–}C_{13})$-heteroaryl, which with the exception of the hydrogen are in each case optionally monosubstituted by amino, substituted amino, amidino, substituted amidino, hydroxyl, carboxyl, carbamoyl, guanidino, substituted guanidino, ureido, substituted ureido, mercapto, methylmercapto, phenyl, 4-chlorophenyl, 4-fluorophenyl, 4-nitrophenyl, 4-methoxyphenyl, 4-hydroxyphenyl, phthalimido, 1,8-naphthalimido, 4-imidazolyl, 3-indolyl, 2-thienyl, 3-thienyl, 2-pyridyl, 3-pyridyl or cyclohexyl, or in which U is $\{CHR(3)\}_n$, where n is 1–8, and R(2) and R(3) together with the atoms carrying these radicals form a mono-, bi- or tricyclic ring system having 2 to 15 carbon atoms;

A is defined as P;

B is a basic amino acid in the L or D configuration, which can be substituted in the side chain;

C is a compound of the formula (IIIa) or (IIIb)

$$\text{G'—G'—Gly} \qquad (IIIa)$$

G'—NH—(CH$_2$)$_p$—CO  (IIIb)

in which
  p is 2 to 8, and
  G' independently of one another is a radical of the formula (IV)

—NR(4)—CHR(5)—CO—  (IV)

in which
  R(4) and R(5) together with the atoms carrying these radicals form a heterocyclic mono-, bi- or tricyclic ring system having 2 to 15 carbon atoms;
E is the radical of a neutral, acidic or basic, aliphatic or alicyclic-aliphatic amino acid;
F is the radical of a neutral, acidic or basic, aliphatic or aromatic amino acid which can be substituted in the side chain, or a direct bond;
K is the radical —NH—(CH$_2$)$_x$—CO— where x=1–4 or a direct bond;
(D)Q is D-Tic, D-Phe, D-Oic, D-Thi or D-Nal, each of which can optionally be substituted by halogen, methyl or methoxy, or a radical of the formula (V) below

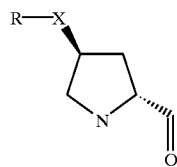  (V)

in which
  X is oxygen, sulfur or a direct bond, and
  R is hydrogen, (C$_1$–C$_8$)-alkyl, (C$_3$–C$_8$)-cycloalkyl, (C$_6$–C$_{14}$)-aryl or (C$_6$–C$_{14}$)-aryl-(C$_1$–C$_4$)-alkyl,
  where the alicycle of formula (V) can optionally be substituted by halogen, methyl or methoxy;
G is defined as G' above or is a direct bond;
M is defined as F;
F' is defined as F, is a radical —NH—(CH$_2$)$_q$—, where q=2 to 8, or, if G is not a direct bond, is a direct bond; and
I is —OH, —NH$_2$ or NHC$_2$H$_5$, wherein I is not directly bonded to D(Q);
or a physiologically tolerable salt thereof.

4. The method as claimed in claim 3 in which said bradykinin antagonist is a peptide of the formula (I), wherein:
Z is as defined above under a$_1$), a$_2$) or a$_3$);
P is a bond or a radical of the formula (II)

—NR(2)—(U)—CO—  (II)

where
  U is CHR(3),
  R(3) is as in claim 2, and
  R(2) is H or CH$_3$, wherein R(2) and R(3) together with the atoms carrying these radicals can form a mono-, bi- or tricyclic ring system having 2 to 15 carbon atoms; and
A is a direct bond;
or a physiologically tolerable salt thereof.

5. The method as claimed in claim 3 in which said bradykinin antagonist is a peptide of the formula (I), wherein:

Z is as defined above under a$_1$), a$_2$) or a$_3$);
P is a bond or a radical of the formula (II)

—NR(2)—(U)—CO—  (II)

where
  R(2) is H or CH$_3$,
  U is CHR(3) and
  R(3) independently of one another is hydrogen, (C$_1$–C$_6$)-alkyl, (C$_3$–C$_8$)-cycloalkyl, (C$_6$–C$_{14}$)-aryl, (C$_3$–C$_{13}$)-heteroaryl, which with the exception of the hydrogen in each case are optionally monosubstituted by amino, substituted amino, hydroxyl, carboxyl, carbamoyl, guanidino, substituted guanidino, ureido, mercapto, methylmercapto, phenyl, 4-chlorophenyl, 4-fluorophenyl, 4-nitrophenyl, 4-methoxyphenyl, 4-hydroxyphenyl, phthalimido, 4-imidazolyl, 3-indolyl, 2-thienyl, 3-thienyl, 2-pyridyl, 3-pyridyl or cyclohexyl, or
  in which R(2) and R(3) together with the atoms carrying these radicals form a mono-, bi- or tricyclic ring system having 2 to 15 carbon atoms;
A is a bond; and
(D)Q is D-Tic;
or a physiologically tolerable salt thereof.

6. The method as claimed in claim 2 wherein said bradykinin antagonist is a peptide of the formula:
H-D-Arg-Arg-Pro-Hyp-Gly-Thi-Ser-D-Tic-Oic-Arg-OH (HOE 140);
para-guanidobenzoyl-Arg-Pro-Hyp-Gly-Thi-Ser-D-Tic-Oic-Arg-OH;
H-D-Arg-Arg-Pro-Hyp-Gly-Phe-Ser-D-HypE(transpropyl)-Oic-Arg-OH;
H-D-Arg-Arg-Pro-Hyp-Gly-Cpg-Ser-D-Cpg-Cpg-Arg-OH;
H-D-Arg-Arg-Pro-Pro-Gly-Thi-Ser-D-Tic-Oic-Arg-OH;
H-Arg(Tos)-Pro-Hyp-Gly-Thi-Ser-D-Tic-Oic-Arg-OH;
H-Arg(Tos)-Pro-Hyp-Gly-Phe-Ser-D-Tic-Oic-Arg-OH;
H-D-Arg-Arg-Pro-Hyp-Gly-Phe-Ser-D-Tic-Oic-Arg-OH;
Fmoc-D-Arg-Arg-Pro-Hyp-Gly-Thi-Ser-D-Tic-Oic-Arg-OH;
Fmoc-Aoc-D-Arg-Arg-Pro-Hyp-Gly-Thi-Ser-D-Tic-Oic-Arg-OH;
Fmoc-ε-aminocaproyl-D-Arg-Arg-Pro-Hyp-Gly-Thi-Ser-D-Tic-Oic-Arg-OH;
benzoyl-D-Arg-Arg-Pro-Hyp-Gly-Thi-Ser-D-Tic-Oic-Arg-OH;
cyclohexylcarbonyl-D-Arg-Arg-Pro-Hyp-Gly-Thi-Ser-D-Tic-Oic-Arg-OH;
Fmoc-Aeg(Fmoc)-D-Arg-Arg-Pro-Hyp-Gly-Thi-Ser-D-Tic-Oic-Arg-OH;
Fmoc-Aeg(Fmoc)-Arg-Pro-Hyp-Gly-Thi-Ser-D-Tic-Oic-Arg-OH;
indol-3-yl-acetyl-D-Arg-Arg-Pro-Hyp-Gly-Thi-Ser-D-Tic-Oic-Arg-OH;
dibenzylacetyl-D-Arg-Arg-Pro-Hyp-Gly-Thi-Ser-D-Tic-Oic-Arg-OH;
or a physiologically tolerable salt thereof.

7. The method as claimed in claim 2 wherein said bradykinin antagonist is a peptide of the formula:
H-D-Arg-Arg-Pro-Hyp-Gly-Thi-Ser-D-Tic-Oic-Arg-OH (HOE 140);
para-guanidobenzoyl-Arg-Pro-Hyp-Gly-Thi-Ser-D-Tic-Oic-Arg-OH;
or a physiologically tolerable salt thereof.

8. The method as claimed in claim 2 wherein said bradykinin antagonist is H-D-Arg-Arg-Pro-Hyp-Gly-Thi- Ser-D-Tic-Oic-Arg-OH (HOE 140), or a physiologically tolerable salt thereof.

9. The method as claimed in claim 3 wherein n is 1–6 when P is a radical of formula (II) and U in formula (II) is {CHR(3)}$_n$.

10. The method as claimed in claim 3 wherein said optional substituted amino of R(3) is —N(A')—Z, in which A' independently of one another is Z, Z being defined as in claim 3 under $a_1$) or $a_2$).

11. The method as claimed in claim 3 wherein said optional substituted amidino of R(3) is —(NH)C—NH—Z, in which Z is defined as in claim 3 under $a_1$) or $a_2$).

12. The method as claimed in claim 3 wherein said optional substituted guanidino of R(3) is —N(A')—C(N(A'))—NH—Z, in which A' independently of one another is Z, Z being defined as in claim 3 under $a_1$) or $a_2$).

13. The method as claimed in claim 3 wherein said optional substituted ureido of R(3) is —C(O)—N(A')—Z, in which A' independently of one another is Z, Z being defined as in claim 3 under $a_1$) or $a_2$).

14. The method as claimed in claim 5 wherein said optional substituted amino of R(3) is —N(A')—Z, in which A' independently of one another is Z, Z being defined as in claim 3 under $a_1$) or $a_2$).

15. The method as claimed in claim 5 wherein said optional substituted guanidino of R(3) is —N(A')—C(N(A'))—NH—Z, in which A' independently of one another is Z, Z being defined as in claim 3 under $a_1$) or $a_2$).

* * * * *

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
      (A) LENGTH: 10 amino acids
      (B) TYPE: amino acid
      (C) STRANDEDNESS: single
      (D) TOPOLOGY: linear (ix) FEATURE:
      (D) OTHER INFORMATION: /note= "1= Xaa is D-Arg; 4= Xaa is
         4Hyp; 6= Xaa is 2-thienylalanyl; 8= Xaa is D-1,2,3,4-
         tetrahydroisoquinolin-3-ylcarbonyl; 9= Xaa is
         cis,endo-octahydroindole-2-carbonyl"

(xi) SEQUENCE DESCRIPTION: SEQ ID NO: 1:

```
Xaa Arg Pro Xaa Gly Xaa Ser Xaa Xaa Arg
1               5                  10
```

(2) INFORMATION FOR SEQ ID NO: 2:

(i) SEQUENCE CHARACTERISTICS:
       (A) LENGTH: 9 amino acids
       (B) TYPE: amino acid
       (C) STRANDEDNESS: single
       (D) TOPOLOGY: linear (ix) FEATURE:
       (D) OTHER INFORMATION: /note= "1= Xaa is para-guanidobenzoyl-
           Arg; 3= Xaa is 4Hyp; 5= Xaa is 2-thienylalanyl; 7= Xaa is
           D-1,2,3,4-tetrahydroisoquinolin-3-ylcarbonyl; 8= Xaa is
           cis,endo-octahydroindole-2-carbonyl"

(xi) SEQUENCE DESCRIPTION: SEQ ID NO: 2:

Xaa Pro Xaa Gly Xaa Ser Xaa Xaa Arg
1               5

(2) INFORMATION FOR SEQ ID NO: 3:

(i) SEQUENCE CHARACTERISTICS:
       (A) LENGTH: 10 amino acids
       (B) TYPE: amino acid
       (C) STRANDEDNESS: single
       (D) TOPOLOGY: linear (ix) FEATURE:
       (D) OTHER INFORMATION: /note= "1= Xaa is D-Arg; 4= Xaa is
           4Hyp; 8= Xaa is D-HypE(transpropyl); 9= Xaa is
           cis,endo-octahydroindole-2-carbonyl"

(xi) SEQUENCE DESCRIPTION: SEQ ID NO: 3:

Xaa Arg Pro Xaa Gly Phe Ser Xaa Xaa Arg
1               5                   10

(2) INFORMATION FOR SEQ ID NO: 4:

(i) SEQUENCE CHARACTERISTICS:
       (A) LENGTH: 10 amino acids
       (B) TYPE: amino acid
       (C) STRANDEDNESS: single
       (D) TOPOLOGY: linear (ix) FEATURE:
       (D) OTHER INFORMATION: /note= "1= Xaa is D-Arg; 4= Xaa is
           4Hyp; 6= Xaa is cyclopentylglycyl; 8= Xaa is
           D-cyclopentylglycyl; 9= Xaa is cyclopentylglycyl"

(xi) SEQUENCE DESCRIPTION: SEQ ID NO: 4:

Xaa Arg Pro Xaa Gly Xaa Ser Xaa Xaa Arg
1               5                   10

(2) INFORMATION FOR SEQ ID NO: 5:

(i) SEQUENCE CHARACTERISTICS:
       (A) LENGTH: 10 amino acids
       (B) TYPE: amino acid
       (C) STRANDEDNESS: single
       (D) TOPOLOGY: linear (ix) FEATURE:
       (D) OTHER INFORMATION: /note= "1= Xaa is D-Arg; 6= Xaa is
           2-thienylalanyl; 8= Xaa is D-1,2,3,4-
           tetrahydroisoquinolin-3-ylcarbonyl; 9= Xaa is
           cis,endo-octahydroindole-2-carbonyl"

(xi) SEQUENCE DESCRIPTION: SEQ ID NO: 5:

Xaa Arg Pro Pro Gly Xaa Ser Xaa Xaa Arg
1               5                   10

(2) INFORMATION FOR SEQ ID NO: 6:

(i) SEQUENCE CHARACTERISTICS:
        (A) LENGTH: 9 amino acids
        (B) TYPE: amino acid
        (C) STRANDEDNESS: single
        (D) TOPOLOGY: linear (ix) FEATURE:
        (D) OTHER INFORMATION: /note= "1= Xaa is Arg(Tos);
            3= Xaa is 4Hyp; 5= Xaa is 2-thienylalanyl; 7= Xaa is
            D-1,2,3,4-tetrahydroisoquinolin-3-ylcarbonyl;
            8= Xaa is cis,endo-octahydroindole-2-carbonyl"

(xi) SEQUENCE DESCRIPTION: SEQ ID NO: 6:

Xaa Pro Xaa Gly Xaa Ser Xaa Xaa Arg
1            5

(2) INFORMATION FOR SEQ ID NO: 7:

(i) SEQUENCE CHARACTERISTICS:
        (A) LENGTH: 9 amino acids
        (B) TYPE: amino acid
        (C) STRANDEDNESS: single
        (D) TOPOLOGY: linear (ix) FEATURE:
        (D) OTHER INFORMATION: /note= "1= Xaa is Arg(Tos); 3= Xaa is
            4Hyp; 7= Xaa is D-1,2,3,4-tetrahydroisoquinolin-
            3-ylcarbonyl; 8= Xaa is cis,endo-octahydroindole-
            2-carbonyl"

(xi) SEQUENCE DESCRIPTION: SEQ ID NO: 7:

Xaa Pro Xaa Gly Phe Ser Xaa Xaa Arg
1            5

(2) INFORMATION FOR SEQ ID NO: 8:

(i) SEQUENCE CHARACTERISTICS:
        (A) LENGTH: 10 amino acids
        (B) TYPE: amino acid
        (C) STRANDEDNESS: single
        (D) TOPOLOGY: linear (ix) FEATURE:
        (D) OTHER INFORMATION: /note= "1= Xaa is D-Arg; 4= Xaa is
            4Hyp; 8= Xaa is D-1,2,3,4-tetrahydroisoquinolin-
            3-ylcarbonyl; 9= Xaa is cis,endo-octahydroindole-
            2-carbonyl"

(xi) SEQUENCE DESCRIPTION: SEQ ID NO: 8:

Xaa Arg Pro Xaa Gly Phe Ser Xaa Xaa Arg
1            5                10

(2) INFORMATION FOR SEQ ID NO: 9:

(i) SEQUENCE CHARACTERISTICS:
        (A) LENGTH: 10 amino acids
        (B) TYPE: amino acid
        (C) STRANDEDNESS: single
        (D) TOPOLOGY: linear (ix) FEATURE:
        (D) OTHER INFORMATION: /note= "1= Xaa is
            9-fluoroenylmethoxycarbonyl-D-Arg; 4= Xaa is 4Hyp;
            6= Xaa is 2-thienylalanyl; 8= Xaa is D-1,2,3,4-
            tetrahydroisoquinolin-3-ylcarbonyl; 9= Xaa is
            cis,endo-octahydroindole-2-carbonyl"

(xi) SEQUENCE DESCRIPTION: SEQ ID NO: 9:

Xaa Arg Pro Xaa Gly Xaa Ser Xaa Xaa Arg
1            5                10

(2) INFORMATION FOR SEQ ID NO: 10:

(i) SEQUENCE CHARACTERISTICS:
        (A) LENGTH: 11 amino acids
        (B) TYPE: amino acid
        (C) STRANDEDNESS: single
        (D) TOPOLOGY: linear (ix) FEATURE:
        (D) OTHER INFORMATION: /note= "1= Xaa is
            9-fluoroenylmethoxycarbonyl-cis,endo-2-azabicyclo
            [3.3.0]octane-3-S-canbonyl; 2= Xaa is D-Arg;
            5= Xaa is 4Hyp; 7= Xaa is 2-thienylalanyl;
            9= Xaa is D-1,2,3,4-tetrahydroisoquinolin-
            3-ylcarbonyl; 10= Xaa is
            cis,endo-octahydroindole-2-carbonyl"

(xi) SEQUENCE DESCRIPTION: SEQ ID NO: 10:

```
Xaa Xaa Arg Pro Xaa Gly Xaa Ser Xaa Xaa Arg
1               5                   10
```

(2) INFORMATION FOR SEQ ID NO: 11:

(i) SEQUENCE CHARACTERISTICS:
        (A) LENGTH: 11 amino acids
        (B) TYPE: amino acid
        (C) STRANDEDNESS: single
        (D) TOPOLOGY: linear (ix) FEATURE:
        (D) OTHER INFORMATION: /note= "1= Xaa is
            9-fluoroenylmethoxycarbonyl-e-aminocaproyl;
            2= Xaa is D-Arg; 5= Xaa is 4Hyp;
            7= Xaa is 2-thienylalanyl; 9= Xaa is
            D-1,2,3,4-tetrahydroisoquinolin-
            3-ylcarbonyl; 10= Xaa is
            cis,endo-octahydroindole-2-carbonyl"

(xi) SEQUENCE DESCRIPTION: SEQ ID NO: 11:

```
Xaa Xaa Arg Pro Xaa Gly Xaa Ser Xaa Xaa Arg
1               5                   10
```

(2) INFORMATION FOR SEQ ID NO: 12:

(i) SEQUENCE CHARACTERISTICS:
        (A) LENGTH: 10 amino acids
        (B) TYPE: amino acid
        (C) STRANDEDNESS: single
        (D) TOPOLOGY: linear (ix) FEATURE:
        (D) OTHER INFORMATION: /note= "1= Xaa is Benzoyl-D-Arg;
            4= Xaa is 4Hyp; 6= Xaa is 2-thienylalanyl; 8= Xaa is
            D-1,2,3,4-tetrahydroisoquinolin-3-ylcarbonyl;
            9= Xaa is cis,endo-octahydroindole-2-carbonyl"

(xi) SEQUENCE DESCRIPTION: SEQ ID NO: 12:

```
Xaa Arg Pro Xaa Gly Xaa Ser Xaa Xaa Arg
1               5                   10
```

(2) INFORMATION FOR SEQ ID NO: 13:

(i) SEQUENCE CHARACTERISTICS:
        (A) LENGTH: 10 amino acids
        (B) TYPE: amino acid
        (C) STRANDEDNESS: single
        (D) TOPOLOGY: linear (ix) FEATURE:
        (D) OTHER INFORMATION: /note= "1= Xaa is Cyclohexylcarbonyl-
            D-Arg; 4= Xaa is 4Hyp; 6= Xaa is 2-thienylalanyl;

8= Xaa is D-1,2,3,4-tetrahydroisoquinolin-3-ylcarbonyl;
                9= Xaa is cis,endo-octahydroindole-2-carbonyl"

(xi) SEQUENCE DESCRIPTION: SEQ ID NO: 13:

Xaa Arg Pro Xaa Gly Xaa Ser Xaa Xaa Arg
1               5                   10

(2) INFORMATION FOR SEQ ID NO: 14:

(i) SEQUENCE CHARACTERISTICS:
        (A) LENGTH: 11 amino acids
        (B) TYPE: amino acid
        (C) STRANDEDNESS: single
        (D) TOPOLOGY: linear (ix) FEATURE:
        (D) OTHER INFORMATION: /note= "1= Xaa is
            9-fluoroenylmethoxycarbonyl-N-(2-aminoethyl)glycyl
            (9-fluoroenylmethoxycarbonyl; 2= Xaa is D-Arg;
            5= Xaa is 4Hyp; 7= Xaa is 2-thienylalanyl;
            9= Xaa is D-1,2,3,4-tetrahydroisoquinolin-
            3-ylcarbonyl; 10= Xaa is cis,endo-
            octahydroindole-2-carbonyl"

(xi) SEQUENCE DESCRIPTION: SEQ ID NO: 14:

Xaa Xaa Arg Pro Xaa Gly Xaa Ser Xaa Xaa Arg
1               5                   10

(2) INFORMATION FOR SEQ ID NO: 15:

(i) SEQUENCE CHARACTERISTICS:
        (A) LENGTH: 10 amino acids
        (B) TYPE: amino acid
        (C) STRANDEDNESS: single
        (D) TOPOLOGY: linear (ix) FEATURE:
        (D) OTHER INFORMATION: /note= "1= Xaa is
            9-fluoroenylmethoxycarbonyl-N-(2-aminoethyl)glycyl
            (9-fluoroenylmethoxycarbonyl; 4= Xaa is 4Hyp;
            6= Xaa is 2-thienylalanyl; 8= Xaa is D-1,2,3,4-
            tetrahydroisoquinolin-3-ylcarbonyl; 9= Xaa is
            cis,endo-octahydroindole-2-carbonyl"

(xi) SEQUENCE DESCRIPTION: SEQ ID NO: 15:

Xaa Arg Pro Xaa Gly Xaa Ser Xaa Xaa Arg
1               5                   10

(2) INFORMATION FOR SEQ ID NO: 16:

(i) SEQUENCE CHARACTERISTICS:
        (A) LENGTH: 10 amino acids
        (B) TYPE: amino acid
        (C) STRANDEDNESS: single
        (D) TOPOLOGY: linear (ix) FEATURE:
        (D) OTHER INFORMATION: /note= "1= Xaa is Indol-3-yl-acetyl-
            D-Arg; 4= Xaa is 4Hyp;6= Xaa is 2-thienylalanyl;
            8= Xaa is D-1,2,3,4-tetrahydroisoquinolin-3-ylcarbonyl;
            9= Xaa is cis,endo-octahydroindole-2-carbonyl"

(xi) SEQUENCE DESCRIPTION: SEQ ID NO: 16:

Xaa Arg Pro Xaa Gly Xaa Ser Xaa Xaa Arg
1               5                   10

(2) INFORMATION FOR SEQ ID NO: 17:

(i) SEQUENCE CHARACTERISTICS:
        (A) LENGTH: 10 amino acids
        (B) TYPE: amino acid -continued

```
        (C) STRANDEDNESS: single
        (D) TOPOLOGY: linear (ix) FEATURE:
          (D) OTHER INFORMATION: /note= "1= Xaa is Dibenzylacetyl-D-Arg
               ; 4= Xaa is 4Hyp; 6= Xaa is 2-thienylalanyl; 8= Xaa is
               D-1,2,3,4-tetrahydroisoquinolin-3-ylcarbonyl;
               9= Xaa is cis,endo-octahydroindole-2-carbonyl"

(xi) SEQUENCE DESCRIPTION: SEQ ID NO: 17:

Xaa Arg Pro Xaa Gly Xaa Ser Xaa Xaa Arg
1               5                   10
```